US009700052B2

(12) United States Patent
Jurenka et al.

(10) Patent No.: US 9,700,052 B2
(45) Date of Patent: Jul. 11, 2017

(54) METHODS AND COMPOSITIONS COMPRISING STEROID HONEY BEE FEEDING INHIBITORS

(71) Applicant: Iowa State University Research Foundation, Inc., Ames, IA (US)

(72) Inventors: Russell A. Jurenka, Ames, IA (US); Matthew O'Neal, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/137,083

(22) Filed: Apr. 25, 2016

(65) Prior Publication Data

US 2016/0309720 A1 Oct. 27, 2016

Related U.S. Application Data

(60) Provisional application No. 62/151,474, filed on Apr. 23, 2015.

(51) Int. Cl.
*A01N 45/00* (2006.01)

(52) U.S. Cl.
CPC .................................. *A01N 45/00* (2013.01)

(58) Field of Classification Search
CPC ................................ A01N 49/00; A01N 45/00
USPC .......................................................... 514/170
See application file for complete search history.

(56) References Cited

U.S. PATENT DOCUMENTS

| | | | |
|---|---|---|---|
| 5,484,587 | A | 1/1996 | Branly et al. |
| 5,571,522 | A | 11/1996 | Munson et al. |
| 5,968,541 | A | 10/1999 | Schroder et al. |
| 6,090,398 | A | 7/2000 | Schroder et al. |
| 6,149,913 | A | 11/2000 | Holmes |
| 6,613,317 | B1 | 9/2003 | Metcalf et al. |
| 7,790,377 | B2 | 9/2010 | Henrich et al. |
| 8,202,552 | B2 | 6/2012 | Gokce et al. |
| 8,343,946 | B2 | 1/2013 | Kramer et al. |
| 2009/0246302 | A1 | 10/2009 | Pathipati et al. |
| 2014/0121184 | A1 | 5/2014 | Willis et al. |

FOREIGN PATENT DOCUMENTS

WO 02058463 A2 8/2002

OTHER PUBLICATIONS

Dinan et al., Biochem. J. (1997), vol. 327, pp. 643-650.*
(Continued)

*Primary Examiner* — Taofiq A Solola
(74) *Attorney, Agent, or Firm* — McKee, Voorhees & Sease, PLC

(57) ABSTRACT

Applicants have discovered novel steroid feeding inhibitors for *Apis* sp. that can be used in connection with traditional insecticide, pesticide, fungicide or other pest management protocols. The rapid decline of *Apis* sp. is devastating to the many crops which rely upon the bees, particularly honey bees (*Apis melliofera*) for pollination. Further it has been postulated that colony collapse disorder, may be the result of unintended ingestion by honey bees of insecticide, pesticide, fungicide compositions applied to nearby feeding sources for the bees. Thus, honey bee feeding inhibitors can be used in a pest management system to prevent unintended consequences to honey bees.

20 Claims, 2 Drawing Sheets

(56) References Cited

OTHER PUBLICATIONS

Wegener et al., J. Insect Physiology (2013), vol. 59, pp. 655-661.*
Hoy, M.A., Agricultural Acarology: Introduction to Integrated Mite Management, Book Review, Journal of Asia-Pacific Entomology, (2012), vol. 15, 1 page.
Mangan, Robert L., "Honey Bee Foraging Preferences, Effects of Sugars, and Fruit Fly Toxic Bait Components", Bio One, Ecology and Behavior, (2009), vol. 102, No. 4, pp. 1472-1481.

* cited by examiner

METHODS AND COMPOSITIONS COMPRISING STEROID HONEY BEE FEEDING INHIBITORS

CROSS-REFERENCE TO RELATED APPLICATIONS

This application claims priority under 35 U.S.C. §119 of provisional application Ser. No. 62/151,474, filed Apr. 23, 2015, which is herein incorporated by reference in its entirety.

FIELD OF THE INVENTION

The present invention relates to the use of novel honey bee feeding inhibitors to prevent honey bees from foraging on crops treated with an insecticide, fungicide, pesticide or other pest control system comprising the same. The feeding inhibitor keeps the bees off flowers and plants that were recently sprayed with the same and prevents the pest control system from adversely affecting honey bee colonies. Compositions including a pesticide, fungicide or insecticide with the feeding inhibitor of the invention are also disclosed as well as the use of the same in managing crop production and honey bee health.

BACKGROUND OF THE INVENTION

Bees play a vital role in the reproduction of plants with entomophilous pollination. The Food and Agriculture Organization of the United Nations (FAO) has estimated that on 100 species of plants that provide 90% of food worldwide, 71 are associated with the bee pollination. Over the last fifty years, the agricultural production, independent of insect pollination, has doubled and agricultural production that requires pollination of insects has increased fourfold, indicating that world agriculture has become more pollinator-dependent. Both the FAO and other independent research organizations in the industry have predicted that the economic value of pollination worldwide agriculture and related sectors is of the order of 180 billion U.S. dollars, of which 32 billion dollars just in the United States. Indeed it is difficult to overstate the role of bees in the commercial production of food.

Honey bees, *Apis mellifera*, are the premier pollinator for the majority of agricultural crops that require pollination. Honey bee health has recently declined across the US due to a number of factors including increasing urbanization and loss of biodiversity, particularly wildflower meadows and "weeds" that provided high quality bee forage, poor nutrition and malnutrition of bees, immunodeficiencies, microbial pathogens including viruses, bacteria, fungi and protozoa, both lethal and sub-lethal exposure to pesticides including insecticides, fungicides and herbicides, beekeeper applied miticides and antibiotics, parasitic mites (*Varroa destructor* and *V. jacobsoni* mites and *Acarapis woodi* tracheal mites), the fungi *Nosema ceranae* and *N. apis*, heavy metals, toxic pollutants, natural plant toxins, biting insects, selective breeding in apiculture and loss of genetic diversity, climate change and increased environmental stresses from drought and cold snaps, and combinations of these factors. Of particular growing concern is a syndrome called Colony Collapse Disorder (CCD). CCD is now approaching 40% colony loss with many beekeepers; large farms, where up to 84,000 beehives are kept in one location, CCD can claim more than 60%. More than ⅓ of all the non-animal food Americans consume is dependent upon pollination from bees. Should this upward trend in bee colony losses continue, the economic and societal expenses could run into the hundreds of billions of dollars.

The main symptoms of CCD are the disappearance of the worker class (resulting in very few or no adult "worker" bees in the hive), a live queen and few to no dead bees on the ground around the colony. Often there is still honey in the hive, immature capped brood bees are present (bees will not normally abandon a hive until the capped brood have all hatched) and the hive contains honey and bee pollen that was not immediately robbed by neighboring bees. The hive is also slow to be robbed by colony pests such as wax moths or small hive beetles. *Varroa* mites, a virus-transmitting parasite of honey bees, have frequently been found in hives hit by CCD. Collapsing colonies typically do not have enough bees to maintain colony brood and have workers that consist of younger adult bees; the progression of symptoms may be rapid or slow (up to two years). The colony may have ample food stores and be reluctant to eat food provided by the beekeeper. See, for example, Honey Bees and Colony Collapse Disorder, United States Department of Agriculture Agricultural Research Service docid=15572 (2013).

The reasons for increasing colony collapse are complex and appear to be the result of multiple factors. Suggested causes include increasing urbanization and loss of biodiversity, particularly wildflower meadows and "weeds" that provided high quality bee forage, poor nutrition and malnutrition, immunodeficiencies, microbial pathogens including viruses, bacteria, fungi and protozoa, both lethal and sub-lethal exposure to pesticides including insecticides, fungicides and herbicides, beekeeper applied miticides and antibiotics, parasitic mites (*Varroa destructor* and *V. jacobsoni* mites and *Acarapis woodi* tracheal mites), the fungi *Nosema ceranae* and *N. apis*, heavy metals, toxic pollutants, natural plant toxins, biting insects, selective breeding in apiculture and loss of genetic diversity, climate change and increased environmental stresses from drought and cold snaps, and combinations of these factors. Research suggests that honey bee diets, parasites, diseases and multiple pesticides interact to have stronger negative effects on managed honey bee colonies, while nutritional limitation and exposure to sublethal doses of pesticides, in particular, may alter susceptibility to or the severity of bee parasites and pathogens.

At present there are not any known treatments or specific solutions for the prevention and treatment of Colony Collapse Disorder, nor methods, techniques or procedures which the beekeeper can put in place with a reasonable expectation of success to protect his hives from the same. In the light of the foregoing, the present invention has the aim of providing a method for the prevention of Colony Collapse Disease or other damage to bees and bee colonies related to the ingestion or exposure to pesticides.

SUMMARY OF THE INVENTION

The present invention relates to the discovery of novel honey bee feeding inhibitors. The feeding inhibitor can be used to prevent honey bees from foraging on crops treated with an insecticide or pesticide comprising the same. The feeding inhibitor also keeps the bees off flowers that were recently sprayed and prevents the pesticides and insecticides from adversely affecting honey bee colonies. This would allow farmers more control in using insecticides and would help to maintain the health of honey bee colonies as well as other types of valuable pollinating insects.

Compositions including a pesticide or insecticide with the feeding inhibitor of the invention are also disclosed as well as the use of the same in managing crop production and honey bee health. According to the invention Applicants have found that certain steroid compounds can deter honey bees from feeding. This is in contrast to traditional bee repellants which rely on the use of volatile compounds, or alkaloids. The steroid backbone containing agents of cucurbitacins and ecdysterone compounds according to the invention may be used as bee deterrents and feeding inhibitors.

For example, in some embodiments, the present invention provides a steroid compound, including one or more of cucurbitacins and/or ecdysterone compounds, wherein the compound exhibits honey bee feeding inhibition. In some embodiments, the feeding inhibitor is used in combination with a pest control system employing pesticides, and the like. In certain embodiments, the steroid compounds exhibit feeding deterrent activity of honey bees or other bee species.

The present invention further provides a method, comprising, providing one or more of feeding inhibitor steroids; and contacting the same with a plant of interest under conditions such that the feeding inhibitor steroids exhibits antifeeding activity. In some embodiments, the steroids exhibit antifeeding activity for *Apis mellifera*. In some embodiments, the plant of interest is a crop plant, such as for example, a food crop (e.g., apples). In certain embodiments, the method further comprises the step of contacting the plant with a known pesticide or insecticide which includes a steroid feeding inhibitor composition.

DEFINITIONS

As used herein, the following terms have the meanings ascribed to them unless specified otherwise.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

As used herein, the term "plant host" refers to a plant or plant part. As used herein, the term "plant part" refers to any portion of a plant or plant substructure, including, but not limited to, leaves (detached or non-detached), roots, stems, fruits, flowers, or protoplast and cell cultures.

As used herein, the term "pesticide" refers to any substance or mixture of substances that prevent, destroy, repel, or mitigate any pest. In some embodiments, the term pesticide applies to insecticides, repellants, anti-feeding agents, herbicides, fungicides, and various other substances used to control pests.

As used herein, the terms "insecticide" and "insecticides" refer to compositions that kill insects or otherwise deter insects from feeding.

As used herein, the term "antifeedant" refers to a composition that prevents an insect or other pest from feeding.

As used herein, the terms "repellent" and "repellents" refer to a composition that repels pests, including insects.

As used herein, the term "biopesticide" refers to a pesticide derived from such natural materials as animals, plants, bacteria, and certain minerals.

As used herein, the term "biochemical" refers to a chemical that occurs naturally in an organism, or an identical substance that has been made artificially.

As used herein, the term "biochemical pesticide" refers to a naturally-occurring substance that controls pests. In some embodiments, biochemical pesticides control pests by insecticidal activity. In other embodiments, biochemical pesticides control pests by a mechanism other than toxicity. Examples include, but are not limited to, sex pheromones that are used as mating disrupters for insect pests, and plant extracts that are used as attractants to lure insect pests to traps or that are used as insect repellents.

As used herein, the term "effective amount," when used in reference to a composition of the present invention, refers to the amount of the composition (e.g., plant extract) necessary to deter the feeding of an insect from the source. When an insect comes into contact with a feeding inhibiting effective amount of a composition, the results are typically that the insects do not feed upon the source which comprises the composition.

"Biologically active", as used herein, refers to a molecule having the structural, regulatory, or biochemical functions of a naturally occurring molecule.

"Industrial crop", as used herein, refers to crops grown primarily for consumption by humans or animals or use in industrial processes (for example, as a source of fatty acids for manufacturing or sugars for producing alcohol). It will be understood that either the plant or a product produced from the plant (for example, sweeteners, oil, flour, or meal) can be consumed. Examples of food crops include, but are not limited to, corn, soybean, rice, wheat, oilseed rape, cotton, oats, barley, and potato plants.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "sample" as used herein is used in its broadest sense. For example, a sample from a plant includes plant extracts and purified plant components or biological molecules.

The phrase "substantially pure" or "isolated" when referring to a peptide or protein, means a chemical composition which is free of other subcellular components of the organism. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon silver staining. For certain purposes high resolution will be needed and HPLC or a similar means for purification utilized.

DESCRIPTION OF THE FIGURES

FIG. 1A is a photo of a grid of 20 bee bowls at the ISU horticulture farm (left).

DETAILED DESCRIPTION OF THE INVENTION

Figures 1A, 1B:
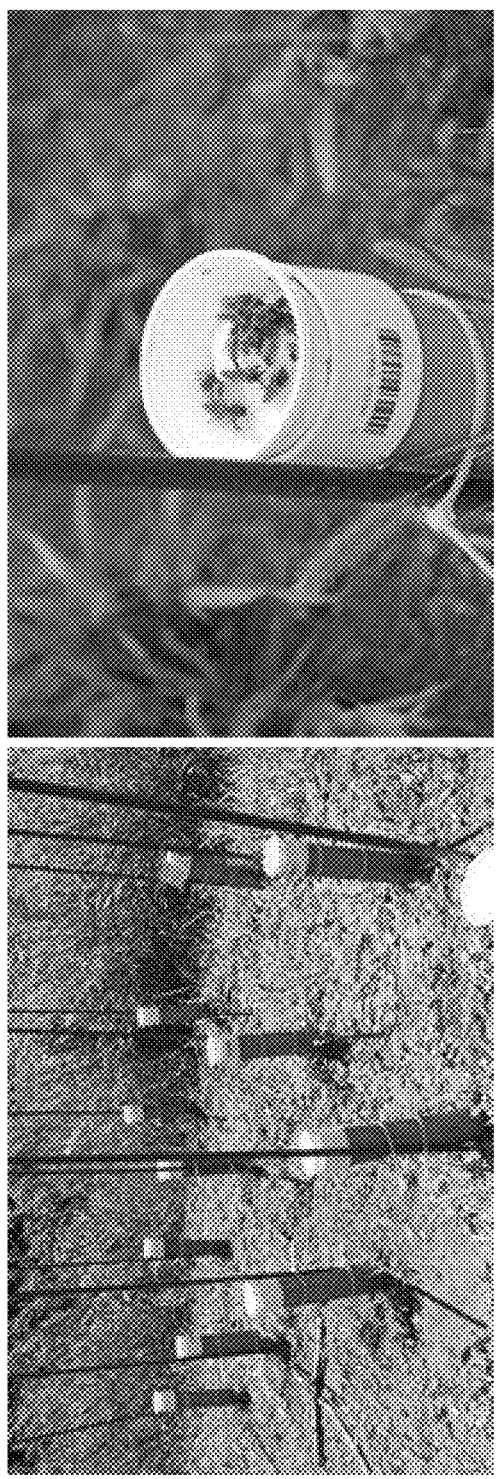
FIG. 1B is a photograph of a bee bowl assigned to the control group with ~15 bees foraging on the corn syrup soaked cotton ball (right).

The invention includes novel feeding inhibitors that can be used in conjunction with traditional pesticides, insecticides or other Integrated Pest Management Systems.

There are many types of pesticides available for controlling pests. Categories include biopesticides, antimicrobials, and pest control devices with many specific categories for types of pests, i.e. acaricides, larvicide, and the like. A variety of broad and specific application pesticides are available from commercial sources. By their very nature, most pesticides create some risk of harm because they are designed to kill or otherwise adversely affect living organisms. At the same time, pesticides are useful to society. Pesticides can kill potential disease-causing organisms and control insects, weeds, and other pests.

Biologically based pesticides, such as pheromones and microbial pesticides, are becoming increasingly popular and often are safer than traditional chemical pesticides. In addition, EPA is registering increasing numbers of reduced-risk conventional pesticides. However, prior to the present invention, biologically based pesticides did not have the potency, e.g., effectiveness, or immediacy of action required to substantially reduce the economic damage of the target pests.

Therefore, in order to balance benefits v. safety, currently the focus of procedures to address pest control uses Integrated Pest Management (IPM) systems. IPM is the use of pest and environmental information in conjunction with available pest control technologies to prevent unacceptable levels of pest damage by the most economical means and with the least possible hazard to persons, property, desirable insects such as pollinating insects, and the environment.

Chemical pesticides include organophosphate pesticides that affect the nervous system by disrupting the enzyme that regulates acetylcholine, a neurotransmitter. Most organophosphates are insecticides. They were developed during the early 19th century, but their effects on insects, which are similar to their effects on humans, were discovered in 1932. Some are very poisonous (they were used in World War II as nerve agents). However, they usually are not persistent in the environment.

Carbamate pesticides affect the nervous system by disrupting an enzyme that regulates acetylcholine, a neurotransmitter. The enzyme effects are usually reversible. There are several subgroups within the carbamates. Organochlorine Insecticides were commonly used in the past, but many have been removed from the market due to their health and environmental effects and their persistence (e.g. DDT and chlordane). Pyrethroid Pesticides were developed as a synthetic version of the naturally occurring pesticide pyrethrin, which is found in chrysanthemums. They have been modified to increase their stability in the environment. Some synthetic pyrethroids are toxic to the nervous system.

Biopesticides, for example, biochemical pesticides, are certain types of pesticides derived from such natural materials as animals, plants, bacteria, and certain minerals. As one example, canola oil and baking soda have pesticidal applications and are considered biopesticides. At the end of 2001, in the U.S. there were approximately 195 registered biopesticide active ingredients being used in 780 products. The three primary types of biopesticides include microbial, plant incorporated protectants, and biochemical pesticides.

Microbial pesticides consist of a microorganism (e.g., a bacterium, fungus, virus or protozoan) as the active ingredient. Microbial pesticides can control many different kinds of pests, although each separate active ingredient is relatively specific for its target pest[s]. For example, there are fungi that control certain weeds, and other fungi that kill specific insects. The most widely used microbial pesticides are subspecies and strains of *Bacillus thuringiensis*, or Bt. Each strain of this bacterium produces a different mix of proteins, and specifically kills one or a few related species of insect larvae. While some Bt's control moth larvae found on plants, other Bt's are specific for larvae of flies and mosquitoes. The target insect species are determined by whether the particular Bt produces a protein that can bind to a larval gut receptor, thereby causing the insect larvae to starve.

Plant-Incorporated-Protectants (PIPs) are pesticidal substances that plants produce from genetic material that has been added to the plant. For example, scientists can take the gene for the Bt pesticidal protein, and introduce the gene into the plant's own genetic material. Then the plant, instead of the Bt bacterium, manufactures the substance that destroys the pest. The protein and its genetic material, but not the plant itself, are regulated by EPA.

Biochemical pesticides are naturally occurring substances that control pests by non-toxic mechanisms. Conventional pesticides, by contrast, are generally synthetic materials that directly kill or inactivate the pest. Biochemical pesticides include substances, such as insect sex pheromones that interfere with mating as well as various scented plant extracts that attract insect pests to traps. Because it is sometimes difficult to determine whether a substance meets the criteria for classification as a biochemical pesticide, EPA has established a special committee to make such determinations.

The feeding Inhibitors of the invention can be used in connection with any of the above pest management systems to deter the effects of the same on bees.

I. Steroid Plant Feeding Inhibitors

Cucurbitacins

The feeding inhibitors of the invention include one or more cucurbitacins. Cucurbitacins have been traditionally used as a feeding stimulant for Diabroticite insects, such as corn rootworm, and are known and described in the art for that purpose (see Metcalf et al., 1987, supra; Rhodes et al. 1980. J. Am. Soc. Hort. vol. 105, pp. 838-842; Metcalf et al. 1981. Cucurbit Genet. Coop. Rep. vol. 4, pp. 37-38; Metcalf, R. L. 1985. Bull. Ill. Natl. Hist. Surv. vol. 33, pp. 175-198; Metcalf and Rhodes, Canadian Patent 1,195,922, 1985; How et al. Environmental Entomol. vol. 5, pp. 1042-1048, all herein incorporated by reference). While the particular implementations that follow describe non-limiting examples involving cucurbitacin B, (alone or in conjunction with other substances), it will be understood that the disclosures contained within this document may equally be applied to other cucurbitacin compounds, as well as their single administration forms, their physiologically active salts or esters, their combinations with their various salts, their tautomeric, polymeric and/or isomeric forms, their analog forms, their derivative forms, and/or their decarboxylation products.

The compounds may be obtained by extraction from Cucurbitaceae plants. The plant material may be dehydrated, then ground into a powdery material, or it may be ground up, the solid material filtered off and the filtrate utilized. The bitter mutant of hawkesbury watermelon (BHW), *Citrullus vulgaris* Schrad, is an example of a plant material which containing cucurbitacins which are effective as a feeding stimulant. The melon may be ground to a pulp and the juice extracted. The extraction may be carried out under pressure as in a cider or hydraulic press, then filtered and utilized directly as a crude liquid extract. It may also be frozen for long-term storage (i.e. months). The juice can also be concentrated by evaporation, spray-drying, freeze-drying or other means to about 3-6% initial weight. Alternatively, cucurbitacins are commercially available through many sources such as Sigma Aldrich, Aktinchem and the like.

The cucurbitacins useful in the present invention are well described in Canadian Patent No. 1,195,922, U.S. Pat. No. 4,880,624, and The Merck Index, 10th ed., p. 2609 (1983). Briefly summarized, plants in the cucurbitaceae order contain small quantities of oxygenated tetracyclic triterpenoid compounds (usually referred to as the cucurbitacins) that are responsible for the bitter taste of the plant tissue. Seventeen of the cucurbitacins have been isolated and identified by letters, namely cucurbitacins A, B, C, D, E, F, G, H, I, J, K, L, O, P, Q, R, in aglycone (somewhat water soluble) or glycoside (very water soluble) forms. The cucurbitacins B, D, E, I aglycone or glycoside forms thereof are preferred feeding inhibitors for use in the present invention.

The cucurbitacin can be added to traditional insecticide of pesticide compositions as a dilute cucurbitacin-containing solid or liquid with a concentration of less than about 0.01 wt % cucurbitacin, as a purified compound, or as a concentrated liquid containing more than about 0.01 wt %, preferably more than about 0.05 wt %, and even more preferably within the range of 0.05-0.5 wt % cucurbitacins. The cucurbitacins can be added as discrete particles homogeneously distributed as a liquid stream. The cucurbitacins or cucurbitacin-containing material are preferably added as a discrete plant tissue particles which contain cucurbitacins, cucurbitacin-containing liquids applied to solid carriers such as a corn cob grit, or introduced as a concentrated liquid that is mixed homogeneously into the matrix with the process liquid used to spray dry the baits. Particularly preferred forms for cucurbitacins are dried powders of dried plant tissues or as a concentrated cucurbitacin solution containing 20-50 wt % solids and about 0.1-0.5 wt % cucurbitacins.

Plant tissues containing the highest levels of cucurbitacins include the roots of the buffalo gourd (*Cucurbita foetidissima*) which, when dried, contain about 0.3% by weight cucurbitacins and fruits of cucurbitacin containing fruits. See, Metcalf Canadian Patent No. 1,195,922 for a list of cucurbitacin-rich plant species useful as cucurbitacin sources for the present invention. Other cucurbitan-containing materials useful for the invention may come from, inter alia, *C. andreana* NAUD, *C. cylindrata* Wats, *C. ecuadorensis* Cutl. and Whit., *C. foetidissima* HBK, *C. gracilior* Bailey, *C. lundelliana* Bailey, *C. martinezii* Bailey, C. okeechobensis Bailey, *C. palmata* Wats., *C. palmeri* Bailey, *C. pedatifolia* Bailey, *C. sororia* Bailey, and *C. texana* Gray.

Buffalo gourd root powder is a preferred source of solid cucurbitacin-containing material for use as the feeding stimulant component in baits of the invention because the root powder contains a significant quantity of starch. This starch acts as a sticking agent when wetted to assist the applied bait particles in adhering to the plant surface. Such adhesion properties are advantageous when bait particles are aerially applied. If desired, however, starch (e.g., food starch) may be added to enhance the sticking effects whether cucurbitacin-containing plant tissues are used or some other form of cucurbitacin.

References herein the "cucurbitacin-containing" shall mean plant tissue solids and either solid or liquid carriers containing at least one of the cucurbitacins A, B, C, D, E, F, G, H, I, J, K, L, O, P, Q, R aglycone or glycoside forms of any of these.

Hydroxyecdysones

The steroid feeding inhibitors of the invention also include one or more hydroxyecdysones.

Ecdysteroids are a group of 2,3,14-trihydroxy-Δ-7-6-ketosteroids. A comprehensive listing of currently-known ecdysteroids, as well as their chemical structures and sources, may be viewed at www.ecdybase.org. Ecdysterone, also variously known as 20-Hydroxyecdysone or "20E," is just one representative type of ecdysteroids. While the particular implementations that follow describe non-limiting examples involving ecdysterone (alone or in conjunction with other substances), it will be understood that the disclosures contained within this document may equally be applied to ecdysteroids other than ecdysterone, as well as their single administration forms, their physiologically active salts or esters, their combinations with their various salts, their tautomeric, polymeric and/or isomeric forms, their analog forms, their derivative forms, and/or their decarboxylation products. In addition the ecdysteroids can be used in their pure form or obtained from plant extracts. The compounds may be obtained by extraction from a variety of plants. The plant material may be dehydrated, then ground into a powdery material, or it may be ground up, the solid material filtered off and the filtrate utilized. Various methods of ecdysteroid extractions from plants have been described in the literature. (See http://ecdvbase.org/presence_of_ecdysteroids.pdf for a listing of literature pertaining to identification of ecdysteroids from plants).

Accordingly, the disclosures contained within this document may apply to ecdysteroids other than ecdysterone, such as by way of non-limiting example, the following ecdysteroids: abutasterone, 25-acetoxy-20-hydroxyecdysone 3-o-; beta;-d-glucopyranoside; acetylpinnasterol; achyranthesterone; ajugacetalsterone a; ajugacetalsterone b; ajugalide e; ajugasterone b; ajugasterone b; ajugasterone c; ajugasterone c3; 22-diacetonide; ajugasterone c 22-ethylidene acetal; ajugasterone c 22-monoacetonide; ajugasterone d; amarasterone a; amarasterone b; asteraster b; atrotosterone a; atrotosterone b; atrotosterone c; blechnoside a; blechnoside b; bombycosterol; bombycoster 3-phosphate; brahuisterone; calonysterone; calvaster a; calvaster b; canescensterone; capitasterone; carpesterol; carthamosterone; carthamosterone a; carthamosterone b; castasterone; cheilanthone a; cheilanthone b; coronatasterone; cyanosterone a; cyasterone; cyasterone 3-acetate; cyasterone 22-acetate; cyasterone 3-monoacetonide; cyathisterone; dacryhainansterone; decumbesterone a; dehydroajugalactone; dehydroajugalactone; dehydroamarasterone b; dehydrocyasterone 2-glucoside; 3-dehydroecdysone; 2-dehydro-3-epi-20-hydroxyecdysone; and/or 22-dehydro-12-hydroxycyasterone.

In addition to the foregoing, the disclosures contained within this document may apply to ecdysteroids other than ecdysterone, such as by way of non-limiting example, the following ecdysteroids: dehydro-20-hydroxyecdysone; 3-dehydro-20-hydroxyecdysone; dehydro-24-2-hydroxymakisterone c; dehydro-12-hydroxy-29-nor-cyasterone; dehydro-12-hydroxy-29-nor-sengosterone; dehydro-12-hydroxy-sengosterone; (28)-dehydromakisterone a; 2-dehydroposterone; 24-dehydroprecyasterone; 2-deoxycastasterone; 22-deoxy-21-dihydroxyecdysone; 22-deoxy-26-dihydroxyecdysone; 2-deoxy-26-dihydroxyecdysone; 3-deoxy-1α 20-dihydroxyecdysone; 2-deoxy-20-dihydroxyecdysone 2-deoxy-polypodine b; 2-deoxyecdysone; deoxyecdysone; 2-deoxyecdysone 3-acetate; 2-deoxyecdysone 22-acetate; 2-deoxyecdysone 22-adenosine-monophosphate; 2-deoxyecdysone 22-benzoate; 2-deoxyecdysone 3-4-(1-β-d-glucopyranosyl)-ferulate; 2-deoxyecdysone 22-β-d-glucoside; 25-deoxyecdysone 22-o-β-d-glucopyranoside; 2-deoxyecdysone 22-phosphate; 2-deoxyecdysone 25-rhamnoside; (5α)-2-deoxy-21-hydroxyecdysone; 2-deoxy-20-hydroxyecdysone; 22-deoxy-26-hydroxyecdysone; 14-deoxy-20-hydroxyecdysone; 2-deoxy-21-hydroxyecdysone; 2-deoxy-20-hydroxyecdysone 25-acetate; 2-deoxy-20-hydroxyecdysone 22-acetate; (5α)-2-deoxy-20-hydroxyecdysone 3-acetate; 2-deoxy-20-hydroxyecdysone 3-acetate; 2-deoxy-20-hydroxyecdysone 22-benzoate; and/or 2-deoxy-20-hydroxyecdysone 3-crotonate.

Additionally, the disclosures contained within this document may further apply to ecdysteroids other than ecdysterone, such as by way of non-limiting example, the following ecdysteroids: 2-deoxy-20-hydroxyecdysone 3-4-(1-β-d-glucopyranosyl-ferulate; 2-deoxy-20-hydroxyecdysone 22-diacetate; 2-deoxy-20-hydroxyecdysone 3-glucoside; 2-deoxy-20-hydroxyecdysone 22-monoacetonide; 2-deoxy-20-hydroxyecdysone 22-phosphate; 22-deoxy-20-hydroxyecdysone 3-phosphate; 2-deoxy-20-hydroxyecdysone-22-glucoside; 2-deoxy-20-hydroxyecdysone-3-o-benzoate; 25-deoxy-20-hydroxyecdysonoic acid; 22-deoxyinokosterone; (5α)-2-deoxyintegristerone a; 2-deoxyintegristerone a; 22-deoxyintegristerone a; (5α)-22-deoxyintegristerone a; 5-deoxykaladasterone 22-acetonide; 20-deoxymakisterone a 24-methyl-ecdysone; 1,2-deoxypolypodine b 3β-d-glucoside; deoxyviperidone 5&alpha:-ket; diauluster a; diauluster b; 22-didehydrotaxisterone; 1,25-dideoxyecdysone; 22-dideoxyecdysone; 22-dideoxy-20-hydroxyecdysone; 22-dideoxy-23-hydroxyecdysone; 22-dideoxy-20-hydroxyecdysone 3β-o-β-d-glucopyranoside; 1,22-dideoxy-20-hydroxyecdysone 3-phosphate; 1,22-dideoxy-23-hydroxyecdysone 3-phosphate; 28-diepi-cyasterone; 8-dihydroajugasterone c; dihydropoststerone; 1 dihydrorubrosterone; (5α)-dihydrorubrosterone; 29-dihydroxycapitasterone; (20r)-1α,20-dihydroxyecdysone; 9β,20-dihydroxyecdysone; 9α,20-dihydroxyecdysone; 1,26-dihydroxyecdysone podecdysone c; 1,26-dihydroxyecdysone 22-acetate; 1,26-dihydroxyecdysone 22-diacetate; 1,26-dihydroxyecdysone 22-diacetate; 1,26-dihydroxyecdysone 26-hemiaceta; diploclidine; ecdysone; ecdysone 3(2)-acetate 22-phosphate; ecdysone 3-acetate; ecdysone 22-acetate; ecdysone 3-acetate 2-phosphate; ecdysone 22-adenosine-monophosphate; ecdysone 3-diacetate 22-phosphate; and/or ecdysone 22-glucoside.

In addition to the above, the disclosures contained within this document may yet further apply to ecdysteroids other than ecdysterone, such as by way of non-limiting example, the following ecdysteroids: ecdysone 22-glycolate; ecdysone 22-linoleate; ecdysone 22-n6-(isopentenyl)-adenosine-monophosphate; ecdysone 25-o-β-d-glucopyranoside; ecdysone 3-o-β-d-glucopyranoside; ecdysone 22-oleate; ecdysone 22-palmitate; ecdysone 22-palmitoleate; ecdysone 22-phosphate; ecdysone 2-phosphate; ecdysone 3-phosphate; ecdysone 22-stearate; ecdysone 22-sulfate; ecdysonoic acid; ecdysteroide; 24-epi-abutasterone; 28-epi-cyasterone; 3-epi-cyasterone; 3-epi-cyasterone 22-acetate; epicyasterone c 5-epi-cyasterone; 3-epi-22-deoxy-26-dihydroxyecdysone; 3-epi-22-deoxy-26-dihydroxyecdysone 2-phosphate; 3-epi-2-deoxyecdysone; 3-epi-2-deoxyecdysone 3-phosphate; 3-epi-2-deoxyecdysone 22-phosphate; 3-epi-2-deoxy-20-hydroxyecdysone; 3-epi-22-deoxy-20-hydroxyecdysone; 3-epi-22-deoxy-20-hydroxyecdysone 2-phosphate; 3-epi-22-deoxy-16.beta. 20-dihydroxyecdysone; 3-epi-22-deoxy-16.beta. 20-dihydroxyecdysone 2-phosphate; 3-epi-26-dihydroxyecdysone; 3-epi-ecdysone; 3-epi-ecdysone 22-phosphate; 25-ep 28-epi-cyasterone c 28-epi-isocyasterone; 3-epi-20-hydroxyecdysone; 3-epi-26-hydroxyecdysone; 14-epi-20-hydroxyecdysone; 22-epi-20-hydroxyecdysone; 3-epi-20-hydroxyecdysone 3-phosphate; 22-epi-14-hydroxypinnaster 2-acetate; 24-epi-makisterone a; 24-epi-pinnatasterone; 3-epi-poststerone; 4-epi-pterosterone; 3-epi-rubrosterone; 28-epi-sengosterone; 22-epoxy-1 25-terahydroxy-ergost-7-en-6-one polyporusterone; 26-epoxy-1 22-tetrahydroxy-ergost-7-en-6-one polyporusterone; 23-epoxy-1 24-tetrahydroxy-ergost-7-en-6-one polyporusterone j; ergosta-22-triene-6-dione; fibraurecdyside makisterone a 3-β-d-glucoside; gerardiasterone; gymnasterone b; herkesterone; 3β 14α 17α 25-hexahydroxy-5α-ergosta-22-dien-6-one; 5-hydroxyabutasterone; 14-hydroxyacetylpinnaster; and/or 25-hydroxyatrotosterone a.

The disclosures contained within this document may still further apply to ecdysteroids other than ecdysterone, such as by way of non-limiting example, the following ecdysteroids: 25-hydroxyatrotosterone b; 14-hydroxycarpester; 23-hydroxycyasterone; 24-hydroxycyasterone; 25-hydroxydacryhainansterone; 1-hydroxy-22-didehydrotaxisterone; 24-hydroxy-28-dihydrocarthamosterone; 20-hydroxyecdysone; 24-hydroxyecdysone; 26-hydroxyecdysone; 11α-hydroxyecdysone; 20-hydroxyecdysone 3(2)-acetate 22-phosphate; 20-hydroxyecdysone 3(2)-phosphate; (5α)-20-hydroxyecdysone epiecdysterone; 20-hydroxyecdysone 22-acetate; 20-hydroxyecdysone 2-acetate; 20-hydroxyecdysone 3-acetate; 20-hydroxyecdysone 3-acetate 2-phosphate; 20-hydroxyecdysone 20-benzoate; (5α)-20-hydroxyecdysone 22-benzoate; 20-hydroxyecdysone 22-benzoate; 20-hydroxyecdysone 22-benzoate 25-glucoside; 20-hydroxyecdysone 2-cinnamate; 20-hydroxyecdysone 2β-d-gluco-pyranoside; 20-hydroxyecdysone 25-β-d-glucoside; 20-hydroxyecdysone 3-β-d-glucoside; 20-hydroxyecdysone 22-diacetate; 20-hydroxyecdysone 22-diacetate; 20-hydroxyecdysone 3; 22-diacetonide; 20-hydroxyecdysone 25-dibenzoate; 20-hydroxyecdysone 22-ethylidene; 26-hydroxyecdysone 22-glucoside; 20-hydroxyecdysone 22-glycolate; 20-hydroxyecdysone 22-linoleate; 20-hydroxyecdysone 22-monoacetonide; 20-hydroxyecdysone 3-monoacetonide; 20-hydroxyecdysone 22-oleate; 240 20-hydroxyecdysone 22-palmitate; 20-hydroxyecdysone 3-p-coumarate; 26-hydroxyecdysone 26-phosphate; 20-hydroxyecdysone 22-phosphate; 26-hydroxyecdysone 2-phosphate; 20-hydroxyecdysone 22-stearate; 20-hydroxyecdysonoic acid; (24r)-24-(2-hydroxyethyl)-20-hydroxyecdysone; 20-hydroxy-24-hydroxymethylecdysone; 25-hydroxypanuosterone; 250 14-hydroxypinnaster; 14-hydroxypinnaster 3-acetate; 26-hydroxypinnatasterone; 26-hydroxypolypodine b; and/or 11a-hydroxypoststerone.

Additionally, the disclosures contained within this document may yet further apply to ecdysteroids other than ecdysterone, such as by way of non-limiting example, the following ecdysteroids: 11α-hydroxyrubrosterone; 5β-hydroxyrubrosterone; hyousterone a; hyousterone b; hyousterone c; 260 hyousterone d; inokosterone; callinecdysone a; inokosterone 26-acetate; inokosterone 22-acetonide; integristerone a; integristerone a 25-acetate; integristerone b;

isocyasterone c; 25-epi-cyasterone; isocyasterone 3-monoacetonide; isovitexirone; kaladasterone; kancollosterone; lesterone; leuzeasterone; limnantheoside a; limnantheoside b; limnantheoside c; makisterone a; makisterone b; makisterone c; podecdysone a; lemmasterone; makisterone d; malacosterone; melandrioside a; 24-methyleneshidasterone; 24-methylshidasterone; muristerone a; 29-norcyasterone; 29-norcyasterone 2-acetate; 29-norcyasterone 3-acetate; 29-norsengosterone; nusilsterone; osladin; 22-oxocyasterone; 22-oxo-20-hydroxyecdysone; palythoalone a; palythoalone b; panuosterone; paristerone; paxillosterone; paxillosterone 22-p-hydroxybenzylidene acetal; 2β,3α,6a,22R,25-pentahydroxy-5b-cholestane; 2β,3β,6a,22,25-pentahydroxy-5b-cholestane; pinnaster; pinnatasterone; podecdysone b; podecdysone b 25-o-β-d-glucoside; polypodine b; (5α)-polypodine b; polypodine b 22-acetate; polypodine b 22-acetonide; polypodine b 22-benzoate; polypodine b 2-cinnamate; polypodine b 3β-d-glucoside; (5α)-polypodine b 3-β-d-glucoside; polypodoaurein; polypodogenin; polypodosaponin; polypodoside a; polypodoside b; polypodoside c; polyporusterone a; polyporusterone b; polyporusterone c; polyporusterone d; polyporusterone e; polyporusterone; polyporusterone; ponasterone a; ponasterone a 22-glycolate; ponasterone b; ponasterone c; ponasterone c 2-cinnamate; ponasteroside a; poststerone; praemixisterone; precyasterone; pterosterone; pterosterone 3-o-β-d-glucopyranoside; and/or pterosterone 24-o-β-d-glucoside.

Finally, the disclosures contained within this document may apply to ecdysteroids other than ecdysterone, such as by way of non-limiting example, the following ecdysteroids: rapisterone; rapisterone b; rapisterone c; rapisterone d; rapisterone d 20-acetate; reptansterone; rhapontisterone punisterone; rhapontisterone; rubrosterone; scabrasterone; schizaeasterone a; schizaeasterone b; sengosterone; serfurosterone a; serfurosterone b; shidasterone; stachysterone d; sidasterone a; sidasterone b; sidisterone; sileneoside a; sileneoside b; sileneoside c; sileneoside d; sileneoside; sileneoside; sileneoside; (5α)-silenoside e; silenosterone 3-dehydro-2-deoxyecdysone; sogdisterone; stachysterone a; stachysterone b; stachysterone b 14,15-epoxide; stachysterone c; taxisterone; tenuifolioside a; tenuifolioside b; 25-tetradeoxyecdysone; 3β,5α,9α,14α-tetrahydroxyergosta-22(e)-dien-6-one; tomentesterone a; tomentesterone b; 25-trideoxyecdysone; trihydroxyecdysone; trihydroxyergosta-22-dien-6-one; trihydroxyergosta-22(e)-dien-6-one; turkesterone; venustone; viperidinone; viperidone; vitexirone; and/or viticosterone e, including any possible esters and salts of the foregoing, consistent with these disclosures.

II. Compositions Employing the Steroid Feeding Inhibitors of the Invention

The steroid feeding inhibitors described herein can be incorporated into compositions and devices useful in controlling insect pests to reduce the impact of the same on bees. For example, the compounds described herein can be incorporated into a composition for application to the environment of the pest, optionally with an agriculturally suitable carrier comprising at least one of a liquid diluent, a solid diluent or a surfactant.

The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be encapsulated or microencapsulated and further formed into a suspension or solid formulation; alternatively the entire formulation of active ingredient can be encapsulated or microencapsulated, e.g., to control or delay release of the active ingredient. Sprayable formulations can be suspended in suitable media and used at preferred spray volumes, e.g., from about one to several hundred liters per hectare. High-strength compositions are primarily used as intermediates (e.g., concentrates) for further formulation (e.g., by dilution).

Active ingredients can include any known pesticide or insecticide, or even fungicide that is applied to plants and that may be in an environment there bees could access the same. The following is a non-limiting list of active insecticides, pesticies or fungicides that may be employed in combination with the steroid feeding inhibitors of the invention.

Avermectin insecticides are a well-known class of insecticides that act by activating chloride channels. They include abamectin and emamectin (most commonly used as its benzoate salt) both of which act by stimulating the release of γ-aminobutyric acid, an inhibitory neurotransmitter, thus causing paralysis and then death of the target insect. Of particular interest to the present invention is emamectin.

Organophosphates are a well-known class of insecticides that act by inhibiting the insect acetylcholinesterase. They include acephate, azamethiphos, azinphos-ethyl or methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos, dicrotophos, dimethoate, dimethylvinphos, disulfoton, EPN, ethion, ethoprophos, famphur, fenamiphos, fenitrothion, fenthion, fosthiazate, heptenophos, isofenphos-methyl, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion. Of particular interest to the present invention is methidathion.

Benzoylureas are a well-known class of insecticides that act by inhibiting chitin biosynthesis meaning that target insect larvae are unable to moult and also cease feeding. They include bistrifluron, chlorfluazuron, diflubenzuron, fluazuron, flucycloxuron, flufenoxuron, hexaflumuron, lufenuron, novaluron, noviflumuron, teflubenzuron and triflumuron. Of particular interest to the present invention is lufenuron.

Neonicotinoids are a well-known class of insecticides that are agonists/antagonists of the nicotinic acetylcholine receptor affecting the synapses in the insect central nervous system. They include acetamprid, clothianidin, dinotefuran, imidacloprid, nitenpyram, thiacloprid and thiamethoxam. Of particular interest to the present invention is thiamethoxam.

In one embodiment, a fungicide is used in the use and method of the invention. In a further embodiment, the fungicide is a strobilurin, in particular, azoxystrobin or trifloxystrobin. Most suitably, the strobilurin is azoxystrobin. In a further embodiment, the fungicide is a triazole. Most suitably, the triazole is difenoconazole.

In one embodiment, an insecticide is used in the use and method of the invention. In a further embodiment, the insecticide is an avermectin, in particular, emamectin or its benzoate salt. In a further embodiment, the insecticide is an organophosphate, in particular, methidathion. In a further embodiment, the insecticide is a benzoylurea, in particular, lufenuron. In a further embodiment, the insecticide is a neonicotinoid, in particular thiamethoxam. Preferably, when lufenuron and thiamethoxam are used, they are used together.

Solid diluents are known in the art, e.g., as described in Watkins, et al., Handbook of Insecticide Dust Diluents and Carriers, 2nd Ed., Dorland Books, Caldwell, N.J. Exemplary solid diluents can include, for example, clays such as bentonite, montmorillonite, attapulgite and kaolin, starch, sugar, silica, talc, diatomaceous earth, urea, calcium carbonate, sodium carbonate and bicarbonate, and sodium sulfate.

Liquid diluents are known in the art, e.g., as described in Marsden, Solvents Guide, 2nd Ed., Interscience, New York, 1950. Exemplary liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tong, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Surfactants are known in the art, e.g., as described in McCutcheon's Detergents and Emulsifiers Annual, Allured Publ. Corp., Ridgewood, N.J.; and in Sisely and Wood, Encyclopedia of Surface Active Agents, Chemical Publ. Co., Inc., New York, 1964. Surfactants can include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers.

In some embodiments, the formulations described herein can contain minor amounts of additives to reduce foam, caking, corrosion, microbiological growth and the like, or thickeners to increase viscosity.

Methods for preparing the formulations described herein are known in the art. For example, solutions, including emulsifiable concentrates, can be prepared by simply mixing the ingredients. Dusts and powders can be prepared, e.g., by blending and, optionally grinding, e.g., using a hammer mill or fluid-energy mill. Suspensions can be prepared, e.g., by wet-milling; see, for example, U.S. Pat. No. 3,060,084. Granules and pellets can be prepared, e.g., by spraying the active material upon preformed granular carriers or by agglomeration techniques. See, e.g., Browning, Chem. Eng., p 14748, (1967); Perry's Chemical Engineer's Handbook, 4th Ed., McGraw-Hill, New York, 1963, pages 8-57 and following, and PCT Publication WO 91/13546. Pellets can be prepared using methods known in the art, e.g., as described in U.S. Pat. No. 4,172,714. Water-dispersible and water-soluble granules can be prepared, e.g., as taught in U.S. Pat. Nos. 4,144,050, 3,920,442 and DE 3,246,493. Tablets can be prepared, e.g., as taught in U.S. Pat. No. 5,180,587 or 5,232,701 and U.S. Pat. No. 5,208,030. See also Woods, "The Formulator's Toolbox—Product Forms for Modern Agriculture" in Pesticide Chemistry and Bioscience, The Food—Environment Challenge, T. Brooks and T. R. Roberts, Eds., Proceedings of the 9th International Congress on Pesticide Chemistry, The Royal Society of Chemistry, Cambridge, 1999, pp. 120-133. See also U.S. Pat. Nos. 7,696,233 and 6,245,816.

In one example, the composition can be delivered in a solid, e.g., as pellets or powder formulation; a semi-solid, e.g., a gel or gellable formulation, e.g., as part of an ant trap; or in a liquid formulation, e.g., in a spray format, and can be used, e.g., to attract or repel ants from a selected area.

In some embodiments, the composition can be provided in a delayed-release composition, so that the composition is released over time. Suitable compositions are known in the art.

In some embodiments, the compounds described herein can be formulated with other ingredients, e.g., attractant ingredients such as insect food (e.g., carbohydrates, cellulose, fats, proteins, and/or any other nutritional components) (see, e.g., U.S. Pat. Nos. 5,152,096; 5,939,061; 6,916,469; and 7,048,918.

In a preferred embodiment, the composition is a liquid composition and is prepared by mixing the steroid feeding inhibitor and insecticide, pesticide of fungicide with concentrate with water to the desired concentration. An effective concentration is from about 0.001% to about 10% (w/v) of steroid feeding inhibitor. The active agent, (insecticide, fungicide, pesticide) and from is added with mixing. An effective active agent concentration is from about 0.025% (w/v) to about 5% (w/v) of aqueous solution. The various additives may also be mixed into the solution at this point. The concentrations of these additives may vary widely, depending on the requirements necessitated by climate, temperature, field conditions, application method, etc., and these amounts are easily determined by one of skill in the art. For example, a useful formulation may be prepared by combining a crude extract of the cucrbitacin or phytoecdysteroid at a concentration of from about 0.001% to about 10% (w/v) with neonicotinoids at a concentration of about 0.0003% to about 0.01%. For example, a concentration of about 0.0003% to about 0.002% (w/v) in a volume of 20 gal/acre applied in an aqueous solution by conventional spray equipment, such as tractor-mounted boom sprayers, backpack sprayers, etc. would be effective, while a concentration of about 0.002% to about 0.01% (w/v) in a volume of 4 gal/acre would be effective for aerial application. A water soluble starch or other thickening agent, such as Mira Sperse 626 (A. E. Staley Mfg. Co., Decatur, Ill.) may be added at a concentration of from about 1% to about 5% (w/v), and a sticker such as Gelva (Monsanto Corp, St. Louis, Mo.) may be added at a concentration of from about 1% to about 3% (w/v).

The composition is applied to target plants (corn, curcubits, peanuts and other agricultural crops attractive to bees) by conventional spraying means. It is applied to flowering plants, for example, at the first sign of flowering. Treatments are applied weekly for about 3 weeks or until pest populations decline below economic injury levels. In corn, treatment may begin at first evidence of adults present on corn or at the time of silking. Weekly treatments continue for about 3 weeks or until the population of adults declines below the economic injury levels. Trap collections and/or counts of living and dead insects in the treated corn may be utilized to estimate population levels.

III. Plants

The methods of the present invention find use in the protection of a variety of plants of interest from pests. The present invention is not limited to a particular plant. The methods and compositions of the present invention are suitable for protecting any plant against pests. In some preferred embodiments, the methods and compositions of the present invention find use in the protection of crop plants against pests. Crop plants include any plant grown for commercial, industrial or food use. Examples include, but are not limited to, food for human consumption (e.g., grains, vegetables, fruits), food for consumption by animals (e.g., animals intended for consumption by humans), crops for industrial use (e.g., generation of industrial oils), etc. In some embodiments, the compositions of the present invention find use in the protection of ornamental plants such as roses or other flowering plants against pests.

The present invention is not limited to use on crop, ornamental, or commercial plants. In some embodiments, plant extracts are utilized to control pests on home gardens or house plants.

The present invention is not limited to a particular application method. Plant insecticidal, pesticidal or fungicidal compositions of varied strengths may be applied to plants of interest using any suitable method. In some embodiments, liquid extracts are sprayed or misted onto plants. For large scale application, aerial application is a desired method. In some embodiments involving small scale application, hand held sprayers are utilized. In other embodiments, the compositions are lyophilized or powdered and a plant extract powder is sprayed or dusted onto plants. In yet other embodiments, plant extract products are applied as granules.

Insecticidal, pesticidal, or fungicidal compositions are applied as needed for pest control in one or more applications. In some embodiments, the compositions are applied before detection of pests. In other embodiments, they are applied at the first sign of appearance of a pest (e.g., larvae or adult stage) and application is continued until all signs of the pest are removed. In yet other embodiments, the compositions are applied at regular intervals throughout the growing season.

All publications and patent applications mentioned in the specification indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are intended only to further illustrate the invention and are not intended to limit the scope of the invention as defined by the claims.

Example 1

We have found that two classes of steroidal compounds that inhibit foraging by honey bees, Apis mellifera. The structure of two of the compounds that were tested is shown below. 20-hydroxyecdysone is the molting hormone of most insects and can be produced by plants as a phytoecdysteroid. Cucurbitacin B is a steroid produced primarily by members of the family Cucurbitaceae. Neither of these compounds have been tested as honey bee feeding inhibitors.

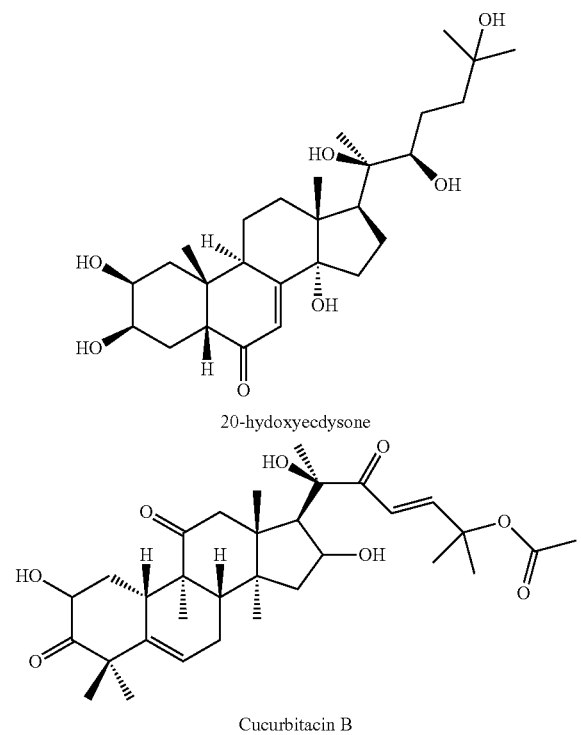

20-hydoxyecdysone

Cucurbitacin B

Assessing Bee Repellency

To test compounds we conducted foraging assays at the ISU Horticulture research farm. A grid of 20 stands were placed about 50 m from 6 honey bee hives. Modified pan traps (referred to as 'Bee bowls') were placed on these stands so they were 20 cm from the ground. Holders were spaced 40 cm apart in an array of 4×5. Bee bowls, painted yellow, contained a cotton ball soaked in corn syrup placed in the center to attract foraging bees. To monitor foraging behavior, we counted the number of bees visiting bee bowls between 1-3 PM for 1 hour. A visit was measured as a bee landing in the cup and remaining in the cup for more than 5 s. During the first week of observations, all bowls contained corn syrup with no test compounds, to attract bees to the site. On June 7 and 10, we observed 164 and 59 visits to the 20 bee bowls during a 1 h observation. On June 11, we placed bee bowls in the holders and treated a sub-set of ten bowls with a plant extract containing phytoecdysteroids. The treated bowls were sprayed with phytoecdysteroids (in a 10 g/l water solution) 3× into the bee bowl using a hand held spray bottle. Most of the solution that entered the bee bowl was absorbed by the cotton ball previously soaked in corn syrup. The other ten bowls were assigned to a control treatment and sprayed 3× with water. Bowls were treated and placed out at 8-9 AM and left to attract bees. Foraging behavior was determined at 1-3 PM for 1 h.

In some treatments a known amount of phytoecdysteroid or pure 20-hydroxyecdysone was tested by adding the compound directly to the corn syrup soaked cotton ball. Each cotton ball was treated with a 1 ml solution in water by adding it directly to the top of the cotton ball with a pipet. FIG. 1A is a photograph of a grid of 20 bee bowls at the ISU horticulture farm (left). FIG. 1B is a bee bowl assigned to the control group with ~15 bees foraging on the corn syrup soaked cotton ball (right).

Bee Bowl Results

The average number of visits to each treatment is shown in Table 1. The treatment of spraying the phytoecdysteroid (Pecd) extract onto the bee bowl greatly inhibited foraging by the bees. Very few bees were observed to land in these cups. They would hover briefly over the cup and then fly off. The results are shown in Table 1.

TABLE 1

Observation of honey bee foraging using bee bowls containing cotton soaked in corn syrup. Values are the average number of bees visiting each cup per 1 h observation. 10 cups per treatment and observation date.

| Date | Water | Pecd 10 g/l | t-test P value |
|---|---|---|---|
| 6/11 | 14.9 | 0.1 | 0.00000023 |
| 6/12 | 8.5 | 0.2 | 0.0011 |
| 6/13 | 6.0 | 0.2 | 0.011 |
| 6/17 | 11.9 | 0.3 | 0.007 |
| 6/19 | 14.5 | 0.4 | 0.002 |
| total | 11.2 | 0.2 | |

To test if purified compounds would inhibit bee foraging, the compounds in 1 ml of water were added directly to the corn syrup soaked cotton ball at various doses. Results indicate that the unpurified phytoecdysteroid inhibited bee foraging down to 5 mg/ml and 1 mg/ml had reduced foraging (Table 2). Similar results were found with the purified phytoecdysteroid where 3 and 1 mg/ml inhibited foraging but 0.2 mg/ml did not (Table 2).

TABLE 2

Observation of honey bee foraging using bee bowls containing cotton soaked in corn syrup and treated with the phytoecdysteroid (Pecd) extract or the purified 20-hydroxyecdysone (ecd). Values are the average number of bees visiting each cup per 1 h observation.

| Unpurified Pecd, mg/cup | Ave visits/cup | # cups | Purified Pecd, mg/cup | Ave visits/cup | # cups |
|---|---|---|---|---|---|
| 10 | 0 | 4 | 10 | 1.0 | 2 |
| 5 | 0 | 4 | 3 | 1.0 | 2 |
| 1 | 3.75 | 4 | 1 | 2.0 | 3 |
| 0.2 | 9.5 | 4 | 0.3 | 11.3 | 3 |
| 0.04 | 9 | 4 | 0 | 8.7 | 3 |

Artificial Flower, Materials and Methods

Figures 2A, 2B:
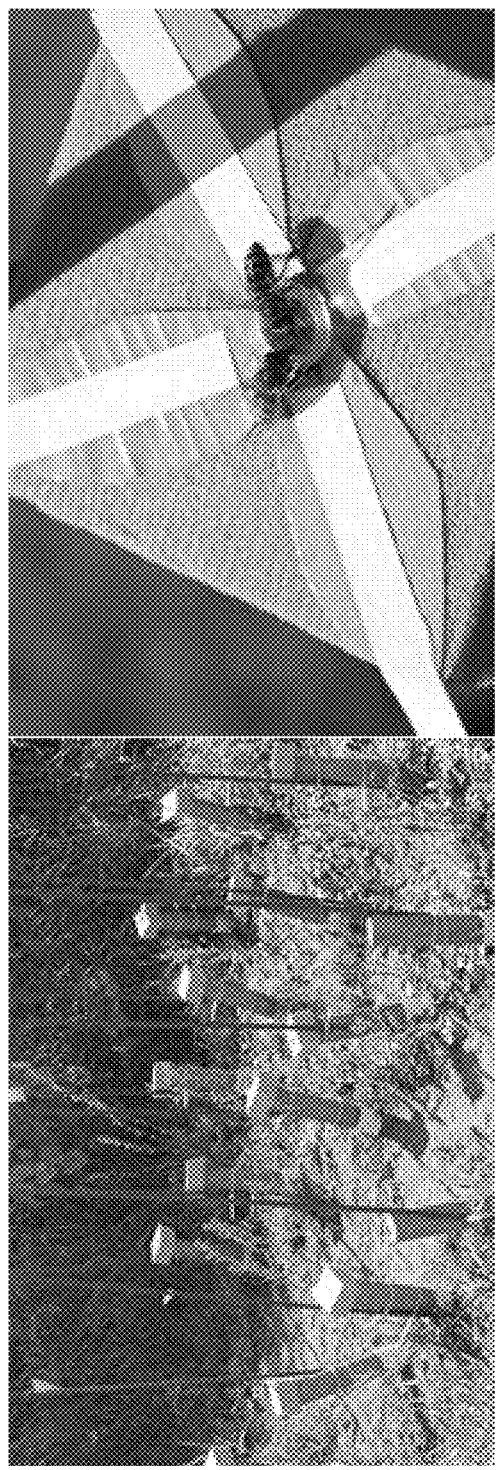
FIG. 2A is a photograph of an array of styrofoam artificial flowers (left).
FIG. 2B is a close up photograph of the top of an artificial flower showing bees foraging (right).

To determine how the phytoecdysteroid inhibits bee foraging, we utilized artificial flowers so that the compounds can be added to a nectar source or sprayed on the surface of the artificial flower. The artificial flowers were made from green florist styrofoam blocks (12 $cm^2$) and petals made from blue and green tape. In the center of the styrofoam block a 2 ml test tube was inserted that contained a 20% sucrose solution in water as a substitute for nectar. The same array of holders was used as in the previous study (FIG. 2).

Compounds tested included the same ones used with the bee bowls. We observed no difference in foraging behavior between control flowers and those with only the surface was sprayed with the phytoecdysteroid (Table 3). We observed a 94% reduction in bee foraging when the phytoecdysteroid was added to the nectar container of the artificial flower. The bees were observed to land on the artificial flower but not forage from the nectar tube when the steroid was sprayed on the surface of the flower and was also present in the nectar tube. This indicates that the inhibitory action of the phytoecdysteroid is due to repellent activity of the steroids when present in the nectar tube. The results are shown in Table 3

TABLE 3

Observation of honey bee foraging using artificial styrofoam flowers with a 2 ml nectar tube containing 20% sucrose. Treatments consisted of a control: the flower surface was sprayed 3x with water and no inhibitor in the nectar tube; Pecd on flower: the flower was sprayed 3x with phytoecdysteroid (Pecd) (10 mg/ml) and no inhibitor in the nectar tube; Pecd on both: the flower was sprayed and contained Pecd in nectar tube; Pecd in nectar: the phytoecdysteroid was placed in the nectar tube. Experiment was conducted using two concentrations of unpurified phytoecdysteroid in the nectar tube (n = 4 for each treatment and concentration).

| | 10 mg/ml | | 5 mg/ml | |
|---|---|---|---|---|
| | feeding | landing | feeding | landing |
| control | 29 | 7 | 42 | 8 |
| Pecd on flower | 41 | 19 | 33 | 3 |
| Pecd on both | 2 | 22 | 1 | 10 |
| Pecd in nectar | 0 | 13 | 2 | 21 |

To determine if the repellent activity occurs in a concentration dependent manner we utilized the artificial flowers treated with various concentrations of the steroids in the nectar tube. In addition to observing the number of honey bees feeding from the nectar tube we measured the amount of nectar consumed after the observation period of about 45 min. The purified phytoecdysteroid was effective at 2.5 and 0.4 mg/ml in reducing the number of honey bees feeding on the nectar compared to lower concentrations. However at 0.4 mg/ml the bees that did forage removed a large amount of nectar. The pure 20-OH-ecdysone was also inhibitory at 1 mg/ml and 0.2 mg/ml with more foraging at the lower concentration. Cucurbitacin B was inhibitory at 0.5 mg/ml but not at 0.1 mg/ml.

TABLE 4

Observation of honey bee foraging using artificial styrofoam flowers with a 2 ml nectar tube containing 20% sucrose. Treatments consisted of various concentrations of purified phytoecdysteroid, 20-hydroxyecdysone, and cucurbitacin B in the nectar tube. n = 4 for each concentration and treatment.

| Conc. mg/ml | Purified phytoecdysteroid | | 20-hydroxyecdysone | | Cucurbitacin B | |
|---|---|---|---|---|---|---|
| | # feeding | Consumed, ml | # feeding | Consumed, ml | # feeding | Consumed, ml |
| 2.5 | 5 | 0.23 | | | | |
| 1 | | | 2 | 0.05 | | |
| 0.5 | | | | | 8 | 0.3 |
| 0.4 | 7 | 1.35 | | | | |
| 0.2 | | | 17 | 0.25 | | |
| 0.1 | 32 | 2 | 56 | 1.7 | 3 | 1.2 |
| 0.025 | 42 | 2 | | | | |
| 0.01 | 56 | 1.7 | 37 | 1.1 | 4 | 1.9 |

Purified phytoecdysteroid refers to the purification of the plant extract. 20-OHecdysone and Cucurbitacin B were purchased in pure form from Chromadex Inc., Irvine, Calif.

To determine if ecdysone is also inhibitory we tested pure ecdysone in the nectar tube at various concentrations. Ecdysone was inhibitory at 1 and 0.1 mg/ml concentrations but not at 0.01 mg/ml. These concentrations were similar to the inhibitory activity of 20-OH-ecdysone and cucurbitacin B.

TABLE 5

Observation of honey bee foraging using artificial styrofoam flowers with a 2 ml nectar tube containing 20% sucrose. Treatments consisted of various concentrations of pure ecdysone purchased from Selleck Chemicals, Houston, TX. n = 4 for each concentration.

| Concentration, mg/ml | Pure ecdsyone | |
| --- | --- | --- |
| | # feeding | Consumed, ml |
| 1 | 0 | 0.2 |
| 0.1 | 0 | 0.3 |
| 0.01 | 24 | 0.8 |
| 0 | 51 | 1.2 |

In summary we have found that several steroids will prevent honey bees from feeding. The steroids tested include the insect growth regulators 20-OH-ecdysone and ecdysone and a steroid produced by cucurbit plants, cucurbitacin B. There are at least 20 other cucurbitacins that have been identified from various plants with similar structures and it is expected that this will have similar inhibitory effects. There are at least 100 phytoecdysteroids that have been identified from various plants and it also expected that these will be inhibitory as well. In essence a variety of compounds with similar chemistries could be screened for activity in preventing honey bee feeding.

What is claimed is:

1. An insecticidal, fungicidal or pesticidal composition that has reduced negative affect on *Apis* species comprising:
    an effective amount of an insecticide, pesticide or fungicide and a steroid feeding inhibitor, wherein the steroid feeding inhibitor is one or more of a compound having a cucurbitacin and/or compound having an ecdysteroid.

2. The composition of claim 1 wherein said cucurbitacin is cucurbitacin A, B, C, D, E, F, O, H, I, J, K, L, O, P, Q, R or aglycone or glycoside forms of the same.

3. The composition of claim 2 wherein said cucurbitacin compound is cucurbitacin B.

4. The composition of claim 1 wherein said ecdysteroid compound is one or more of 2, 3, 14-trihydroxy-Δ-7-6-ketosteroid compounds.

5. The composition of claim 4 wherein said 2, 3, 14-trihydroxy-Δ-7-6-ketosteroid is 20-hydroxyecdysone.

6. The composition of claim 1 further comprising one or more of the following: adherents, thickeners, emulsifiers, stabilizers, preservatives, surfactants, anti-foam agents and buffers.

7. The composition of claim 1, wherein said insecticide, pesticide, or fungicide is present in an amount from about 0.025% (w/v) to about 5% (w/v) of aqueous solution.

8. The composition of claim 3, wherein said toxicant is present in an amount from about 0.1% (w/v) to about 0.5% (w/v) of aqueous solution.

9. The composition of claim 5, wherein said steroid feeding inhibitor is present in an amount of from about 0.05% (w/v) to about 5% (w/v).

10. The composition of claim 1, wherein said composition further comprises a carrier.

11. The composition of claim 1, wherein said insecticide is neonicotinoid.

12. The composition of claim 1, wherein said compound having a cucurbitacin and compound having an ecdysteroid is a phytoecdysteroid, 20-hydroxyecdysone, cucurbitacin B, and ecdysone.

13. A method of inhibiting bee feeding on plants comprising:
    applying to said plants a composition comprising a one or more of a compound having cucurbitacin and/or compound having an ecdysteroid and a carrier.

14. The method of claim 13 wherein said applying is by spraying.

15. The method of claim 13 wherein said carrier is water.

16. The method of claim 13 wherein said plants are crop, ornamental, or commercial plants.

17. The method of claim 13 wherein said composition further comprises an insecticide, pesticide or fungicide.

18. A method for preventing colony collapse disorder in a bee hive comprising:
    treating any nearby crop, ornamental, or commercial plants with an insecticide, pesticide, or fungicide composition that includes a steroid feeding inhibitor, wherein the steroid feeding inhibitor is one or more of a compound having a cucurbitacin and/or a compound having an ecdysteroid.

19. The method of claim 18 wherein said compound having a cucurbitacin includes cucurbitacin A, B, C, D, E, F, G, H, I, J, K, L, O, P, Q, or R or aglycone or glycoside forms of the same, or a 2,3,14-trihydroxy-Δ-7-6-ketosteroid.

20. The method of claim 18 wherein said compounds and ecdysteroids are purified from their plant sources.

* * * * *